United States Patent [19]

Tenygl

[11] Patent Number: 4,661,210
[45] Date of Patent: Apr. 28, 1987

[54] METHOD AND APPARATUS FOR ELECTROCHEMICAL ANALYSIS OF SOLUTIONS

[75] Inventor: Jiri Tenygl, Prague, Czechoslovakia

[73] Assignee: Ceskoslovenska akademie ved, Praha, Czechoslovakia

[21] Appl. No.: 864,283

[22] Filed: May 16, 1986

[30] Foreign Application Priority Data

May 16, 1985 [CS] Czechoslovakia .................... 3527-85

[51] Int. Cl.$^4$ ...................... G01N 27/30; G01N 27/50
[52] U.S. Cl. .................................. 204/1 T; 204/409; 204/413
[58] Field of Search .............. 204/413, 1 T, 1 M, 405, 204/409

[56] References Cited

U.S. PATENT DOCUMENTS 4,072,594  2/1978  Outsuka et al. ................. 204/413 X
4,601,792  7/1986  Tenygl ................................. 204/1 T Primary Examiner—G. L. Kaplan

[57] ABSTRACT

The invention pertains to a method and apparatus for the electrochemical analysis of solutions which comprises the measurement of an electric signal between a mercury column in a capillary and a reference electrode which are in contact with the analyzed solution sucked into the capillary. The mercury column in the capillary pulsates during the measurement. Current or voltage may be measured as the electric signal. An apparatus for the analysis of microliter volumes of solutions comprises a vessel for the analyzed solution provided with an inlet and outlet of the analyzed solution and a reference electrode, one end of a capillary is connected to the vessel for the analyzed solution and the other end of the capillary is connected to means for suction and ejection of mercury. A pulsator is attached to the capillary for moving the column of mercury and an electric contact is built into the capillary in contact with the mercury column. A measuring device is provided to measure the electric signal between the reference electrode and the electric contact.

2 Claims, 1 Drawing Figure

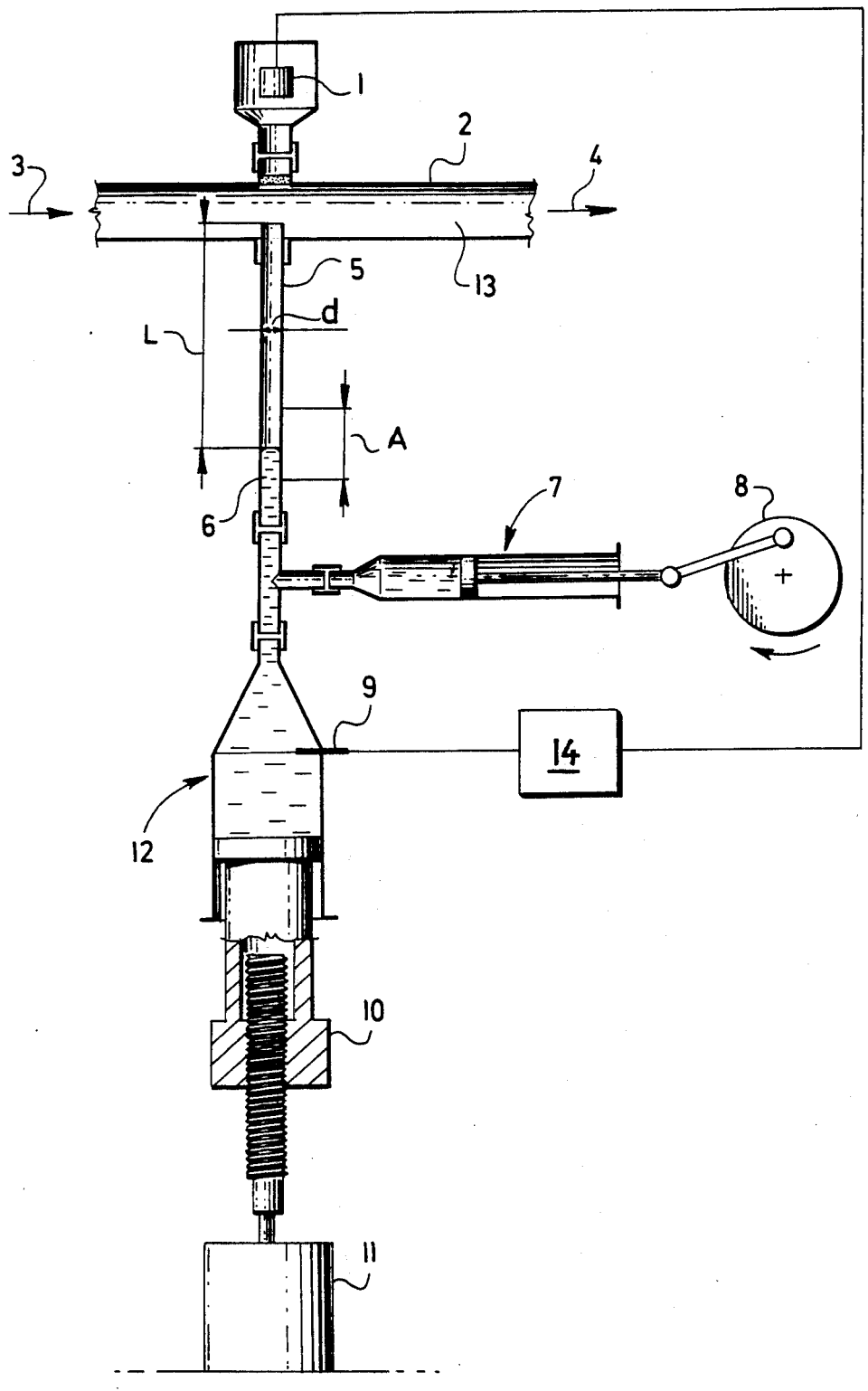

METHOD AND APPARATUS FOR ELECTROCHEMICAL ANALYSIS OF SOLUTIONS

BACKGROUND OF THE INVENTION

The invention pertains to a method and apparatus for the electrochemical analysis of solutions.

Electrochemical analysis based on the principle of voltametry and coulometry is presently performed with mercury electrodes of various design, for example, with the dropping mercury electrode, static mercury drop, mercury pool electrode, and several others. The analysis is carried out in cells of various shape. One of the fundamental requirements of the design of cells is the maintenance of a constant convention of the analyzed solution in the cell. This is achieved by various types of stirrers, by the flow of the analyzed solution along the electrode, or by motion of the electrode, e.g. by its rotation. Further problems arise with metering of the sample and the design of the cell in the analysis of small volumes of solutions. Therefore, the measurement is carried out with utilization of new measuring principles, for example, in a stream of sample, which is segmented with gas bubbles, or in a stream of a carrier electrolyte into which a metered amount of sample is injected (flow-injection analysis). But the equipment for performing the above mentioned new measuring principles is rather complicated and costly.

SUMMARY OF THE INVENTION

The method of electrochemical analysis according to the invention avoids some disadvantages of the hitherto used analytical methods. The method comprises the suction of an analyzed solution into a capillary, which is completely filled with mercury at the beginning of measurement, by the movement of the mercury column formed in the capillary. The analyzed solution and the measurement of current or potential is performed between the mercury column in the capillary, analyzed solution sucked in the capillary and reference electrode being in contact with the analyzed solution, whereas the mercury column in the capillary pulsates forward and backward during the measurement. An apparatus for performing the method according to the invention comprises a cell for the analyzed solution provided with an inlet and outlet of the analyzed solution and a reference electrode, whereas the capillary is connected by one end to the cell for the analyzed solution and by the other end to means for suction and ejection of mercury. A pulsator is attached to the capillary and an electric contact is built into the capillary. A measuring device is designed to measure the electric signal between the reference electrode and the electric contact.

The advantage of the method according to the invention are achieved by the use of a capillary which not only restricts the area of the indication electrode but also serves as a cell with a very small volume and a precisely defined geometry. The analyzed solution adheres to the walls of capillary due to capillary forces and, consequently, a spontaneous and irreproducible convection, caused by changes in density or temperature of the analyzed sample, is suppressed. The volume of the analyzed sample sucked into the capillary may be determined and measured with a high accuracy from the position of mercury column in the capillary. The sucked analyzed sample may also be quantitatively ejected from the capillary by moving the mercury column. The amount of analyzed solution which adheres to the capillary walls is so small that it does not substantially affect the result of the subsequent analysis. There is, therefore, no need to rinse the cell with the supporting electrolyte or analyzed solution between subsequent determinations.

Another advantage of the method according to the invention is attained by forward and backward pulsation of the mercury column in the capillary. The pulsation of the mercury column provides a defined and reproducible convection of mercury and also of a column of the analyzed solution. Agitation of the mercury column occurs by pulsation of the column forwards and backwards. In this way, passivating layers on the surface of mercury column are broken and also mercury inside the mercury column is agitated, which leads to the dilution of amalgams formed on the surface of mercury meniscus by reduction of metal ions. The surface of the mercury column which serves as the indication electrode is recovered in this way.

The pulsation of the mercury column forwards and backwards is also transferred on the column of analyzed solution sucked into the capillary. This provides its reproducible agitation and causes a defined dilution of a layer of depleted solution, which was in contact with the surface of the mercury column, by other layers of the solution in capillary. This effect enables one to predict the time course of the concentration decreases of the species to be determined in the analyzed solution in the capillary by extrapolation of the electric signal, i.e. of current or voltage, obtained by the measurement between the mercury column in the capillary and the reference electrode.

Besides the above described recovery of the surface of the mercury column caused by its forward and backward motion, the surface of mercury meniscus can be recovered by a periodic polarization towards positive potentials which leads to anodic dissolutions of deposited amalgams.

If the contamination is high, the contaminated mercury may be completely removed by ejection from the capillary into a flow of analyzed solution. The contaminated mercury may be retained from the analyzed solution in a mercury trap which is not shown in the accompanying drawing.

BRIEF DESCRIPTION OF THE DRAWINGS

With these and other objects in view, which will become apparent in the following detailed description, the present invention, which is shown by example only, will be clearly understood in connection with the accompanying drawing, wherein:

The single FIGURE is a side elevation view, partially in section and partially schematic, of the apparatus of the invention.

DESCRIPTION OF THE PREFERRED EMBODIMENT

The apparatus for performing the method according to the invention is diagrammatically shown in the appended drawing. It comprises of a reference electrode 1, which is connected through a salt bridge with the cell 2 for analyzed solution 13. The cell 2 is provided with an inlet 3 and outlet 4, through which the analyzed solution 13 passes. A capillary 5, made from glass or transparent plastics, is connected to the cell 2 for the analyzed solution 13. The drawing shows the apparatus in the operation position when the capillary 5 is filled with the analyzed solution 13 and mercury 6. A pulsator 7 and means for ejection and suction of mercury 12 are connected to the capillary 5. The pulsator 7 and pulsator drive 8 are shown as a cylinder with a piston driven by a crankshaft of a small motor. However, other types of pulsators may be used, for example, an elastic membrane which is at one side mechanically or electromagnetically pushed while its other side is in contact with mercury 6. The means for ejections and suction of mercury 12 is also depicted as a piston with a cylinder which displacement forwards and backwards is provided by a screw and nut 10 driven with a stepping motor 11. Other types of equipment can also be used, for example, a membrane operated electromagnetically or mechanically.

An electric contact 9 reaches into mercury 6 and current or voltage is measured with a measuring device 14 between the reference electrode 1 and the meniscus of mercury 6 in the capillary 5 which meniscus and electrode are conductively connected with the analyzed solution 13.

The inner diameter d of capillary 5 is chosen in the range of 0.005 mm to 3 mm depending on the volume of the analyzed solution, the way of application and the principle of electrochemical measurement. For the analysis of a very small volume of analyzed solution on the order of about $10^{-9}$ liters, a capillary with d=0.0005 to 0.01 mm is chosen, for a common analysis, d=0.05 to 0.7 mm, and for the analysis of contaminated solutions, d=0.07 to 3 mm.

The amplitude A and frequency f (not shown) of the foward-backward motion of mercury 6 in the capillary 5, and the position L of the meniscus or mercury column in the capillary 5 measured after suction of the analyzed solution from the orifice of capillary 5 into the cell 2 are chosen in accordance with the measuring method used and the type of sample analyzed and may be in the ranges A=0.01 d to 100 d, f=0.05 to 50 Hz, and L=0.1 d to 1000 d.

The usual inner shape of the capillary 5 in the direction of its longitudinal axis is cylindric. However, conic capillaries or capillaries with one or several blown cavities of a spherical shape or a shape of rotation ellipsoid may also be used. The conic shape of the inner space of capillary or the blown cavities contribute to a better agitation of mercury and the analyzed solution inside the capillary.

EXAMPLES OF MEASUREMENT BY THE METHOD AND APPARATUS OF THE INVENTION.

EXAMPLE 1

Continuous voltametric determination of nickel in waste waters:

A rinse water drained from plants for galvanic plating with the Watts bath is essentially the approximately, thousandtimes diluted plating bath which contains about $1 \times 10^{-3}$M $Ni^{2+}$. A sample of rinse water is mixed with the solution having composition 0.1 N $NH_4OH$, 0.1N $NH_4Cl$, 0.1N $Na_2SO_3$ and flows through the inlet 3 into the cell 2 and leaves through the outlet 4. Before starting the analysis, the stepping motor 11 is switched on and displaces, by means of the screw with nut 10, the piston in the means for ejection and suction of mercury 12 until the capillary 5 is completely filled with mercury and about 5 microliters of mercury overflows from the capillary into the cell 2. The stepping motor 11 is then stopped and the sense of its rotation is changed. The piston in the means for ejection and suction of mercury moves in the opposite direction and sucks mercury and the analyzed solution 13 into the capillary 5. The stepping motor 11 revolves until the level of mercury L in the capillary 5 is lowered for four values of the inner diameter d of the capillary 5 below its orifice. The capillary 5 has inner diameter 1.5 mm; amplitude A of the pulsator is set to the value 4d. The frequency f of the foward-backward motion of mercury is set to 10 Hz. The drive pulsator 7 is then switched on. By the action of the pulsator 7, the level of mercury L in the capillary 5 shifts from the lower position L=4d below the capillary orifice to its upper position which is at the level of capillary orifice L=0. The analyzed solution 13 is sucked from the cell 2 into the capillary 5 by the motion of mercury 6 forwards and ejected from the capillary 5 into the cell 2 at the reverse motion of mercury 6. Voltage E=1.4 V is connected between the reference saturated calomel electrode 1 and the electric contact 9 with the negative pole connected to the electric contact 9 and the passing current which is proportional to the concentration of $Ni^{2+}$ in the analyzed solution is measured by measuring device 14.

EXAMPLE 2

Determination of $Cd^{2+}$ content in batch samples:

The cell 2 is charged with about 5 ml of the analyzed solution 13 containing about $1 \times 10^{-2}$M $Cd^{2+}$. The equipment is prepared for analysis in the same way as it is described in example 1 above. Mercury is ejected from the capillary until about 5 microliters overflows into the cell. The mercury level is then lowered to L=100d below the capillary orifice. A capillary 5 with inner diameter d=0.5 mm is used. The pulsator 7 is switched on at the amplitude set to A=1d and frequency f=5 Hz. The voltage E between the reference electrode 1 and the electric contact 9 is stepwise varied as described below. The negative pole is connected to the electric contact 9. The passing electric charge, i.e. the integral of electrolysis current I vs. time T is measured.

Measurement at voltage E=0.4 V

Only reduction of the dissolved oxygen occurs at this voltage. The electrolysis is carried out for 5 minutes. Air oxygen dissolved in the solution is reduced during electrolysis and the current I of electrolysis gradually deceases. Within 5 minutes it decreases to about 5% of its value in time T=0 at the beginning of the electrolysis. In this way, oxygen is removed from the solution to such extent that it does not substantially interfere in the following measurement of cadmium.

Measurement of voltage E=1.0 V

At this voltage, reduction of $Cd^{2+}$ occurs according to the reaction $Cd^{2+}+2e=Cd$. The deposited reduced cadmium dissolves in mercury and forms cadmium amalgam. The passing electric charge is integrated for 3 min. It is proportional to the amount of cadmium in the column of solution in the capillary above mercury level and thus also in the analyzed solution in the cell. The volume of this solution column in the capillary depends on d, L, and A and can be calculated. But it can be determined in an easy way by calibration with a standard solution. It is essential that this volume is well reproducible if the same experimental conditions are maintained.

Measurement at voltage E=0 (the disconnected voltage source)

After completing the electrolysis at E=1.0, the inserted voltage is disconnected and a voltmeter with a high input impedance (at least 1 Mohm) is connected to the reference electrode and the current supply. The potential difference between the mercury column in the capillary and the reference electrode is measured in this way. The potential difference is a logarithmic function of the concentration of deposited cadmium amalgam and thus also a logarithmic function of concentration $Cd^{2+}$ in the analyzed solution. The concentration $Cd^{2+}$ — in the analyzed solution is calculated from the Nernst equation. The exact values of concentration $Cd^{2+}$ including the geometry of the capillary used are determined from the result of calibrating determinations performed with standard solutions. A supplementary value about the concentration of cadmium ions in the analyzed solution is obtained in this way. Measurement of the potential difference as it is described above is particularly suitable for the determination of low concentration below $1\times10^{-4}M\ Cd^{2+}$.

Measurement at voltage E=0.1 V

After the potential difference has been measured, the voltage 0.1 V is connected between the reference electrode and the current supply and the passing current is integrated for 5 min. At this voltage, cadmium amalgam is dissolved from mercury in the capillary. The passing electric charge is proportional to the amount of cadmium amalgam deposited during the measurement at E=1.0 V and thus also to the concentration of $Cd^{2+}$ in the analyzed solution and a further supplementary value about the concentration of $Cd^{2+}$ ions is obtained in this way. An advantage of this anodic dissolution, in addition to the above mentioned obtaining of the supplementary value, consists in purification of mercury in the capillary by the anodic dissolution from the deposited cadmium amalgam or also from other amalgamable metals. Cadmium or other amalgamable metals are dissolved from the mercury column in the capillary into the analyzed solution in the capillary.

The measurement is completed by this procedure. The drive of the pulsator is stopped and the stepping motor is switched on and displaces the piston of the means for mercury ejection until the mercury level in the capillary reaches just to the orifice of the capillary into the cell. Overflow of mercury from the capillary into the cell is not necessary, because it was previously purified by anodic dissolution. During the displacement of mercury in the capillary, the analyzed solution is ejected from the capillary into the cell. The capillary is thus cleaned from the analyzed solution. The equipment is prepared in this way for further measurement.

I claim:

1. Method of electrochmeical analysis of solutions using the principles of voltammetry, coulometry and potentiometry by measuring an electric signal between a mercury electrode kept in contact with an analyzed solutions and a reference electrode immersed into the analyzed solution, comprising the following steps:

introducing of the mercury into a capillary forming thus a mercury column electrode., suction of the analyzed solution in part of the capillary by the movement of the mercury column, bringing the mercury column into pulsating motion, applying an electrical signal across the mercury column electrode and reference electrode, and measuring the electric signal between the mercury column, analyzed solution sucked into the capillary and the reference electrode.

2. An apparatus for performing electrochemical analysis of solutions using the principles of voltammetry or coulometry by measuring the electric signal between a mercury electrode and a reference electrode brought into the contact with an analyzed solution comprising a cell provided with an inlet and outlet through which the analyzed solution passes, a reference electrode located in the cell and in conductive contacat with the analyzed solution, a capillary for containing a column of mercury and the analyzed solution, said capillary being with one of its ends connected to the cell, a source of mercury connected to the capillary, means for ejection and suction of the column of mercury, said means being connected to the other end of the capillary, means for pulsating movement of the column of mercury within the capillary, an electric contact conductively connected to the column of mercury, means for supplying an electrical signal to the electric contact and the reference electrode, and a measuring device electrically connected to the reference electrode and the electric contact for measuring the electric signal between the reference electrode and the electric contact.

* * * * *